US008369950B2

(12) United States Patent
Rawat et al.

(10) Patent No.: US 8,369,950 B2
(45) Date of Patent: Feb. 5, 2013

(54) IMPLANTABLE MEDICAL DEVICE WITH FRACTAL ANTENNA

(75) Inventors: Prashant Rawat, Blaine, MN (US); Jeffrey A. Von Arx, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1953 days.

(21) Appl. No.: 11/262,157

(22) Filed: Oct. 28, 2005

(65) Prior Publication Data

US 2007/0100385 A1 May 3, 2007

(51) Int. Cl.
*A61N 1/00* (2006.01)
(52) U.S. Cl. ......................................... 607/32
(58) Field of Classification Search .............. 607/36–38, 607/32; 128/897
See application file for complete search history.

(56) References Cited

U.S. PATENT DOCUMENTS

| | | | |
|---|---|---|---|
| 5,117,825 A * | 6/1992 | Grevious | 607/32 |
| 5,861,019 A * | 1/1999 | Sun et al. | 607/60 |
| 6,104,349 A * | 8/2000 | Cohen | 343/702 |
| 6,115,634 A * | 9/2000 | Donders et al. | 607/32 |
| 6,452,553 B1 * | 9/2002 | Cohen | 343/702 |
| 6,456,256 B1 * | 9/2002 | Amundson et al. | 343/873 |
| 6,476,766 B1 * | 11/2002 | Cohen | 343/700 MS |
| 6,525,691 B2 * | 2/2003 | Varadan et al. | 343/700 MS |
| 6,729,336 B2 * | 5/2004 | Da Silva et al. | 128/897 |
| 7,015,868 B2 | 3/2006 | Puente Baliarde et al. | |
| 2002/0113739 A1 * | 8/2002 | Howard | 343/702 |
| 2002/0123776 A1 * | 9/2002 | Von Arx et al. | 607/60 |
| 2002/0149519 A1 | 10/2002 | Varadan et al. | |
| 2002/0149521 A1 * | 10/2002 | Hendler et al. | 343/700 MS |
| 2002/0175874 A1 * | 11/2002 | Eason | 343/770 |
| 2004/0176811 A1 * | 9/2004 | Von Arx et al. | 607/32 |
| 2005/0195112 A1 * | 9/2005 | Baliarda et al. | 343/700 MS |
| 2005/0203583 A1 * | 9/2005 | Twetan et al. | 607/36 |
| 2005/0237238 A1 | 10/2005 | Rahola | |
| 2005/0251032 A1 | 11/2005 | Smith | |
| 2006/0077101 A1 | 4/2006 | Puente Baliarda et al. | |

(Continued)

FOREIGN PATENT DOCUMENTS

| | | |
|---|---|---|
| EP | 1890765 | 2/2008 |
| WO | WO-2006131302 A1 | 12/2006 |

OTHER PUBLICATIONS

Soontornpipit, P., et al., "Design of Implantable Microstrip Antenna for Communication With Medical Implants", *IEEE Transactions on Microwave Theory and Techniques,* 52(8), (2004), 1944-1950.
"Fractus designs, develops and manufactures antennas for the mobile handset, wireless device and telecoms infrastructure markets worldwide.", http://www.fractus.com/technology.htm, (2005),2 p.

(Continued)

*Primary Examiner* — George Manuel
(74) *Attorney, Agent, or Firm* — Schwegman Lundberg & Woessner, P.A.

(57) ABSTRACT

An apparatus and method for enabling an implanted fractal antenna for radio frequency communications between an implantable medical device and an external device. The fractal antenna may be disposed within or outside of a header assembly of the device housing. Various examples include a three dimensional patterned cylinder usable as a tissue anchor or stent. In another embodiment the antenna may be cast, molded, stamped, punched, milled, laser cut, etched or other methods to form a fractal pattern in conductive media. In another embodiment the antenna may be formed of a printed circuit board (PCB) either with or without an included ground reference plane. In another embodiment the antenna may be formed in a fractal pattern and then wrapped around a part of the implantable device.

17 Claims, 5 Drawing Sheets

U.S. PATENT DOCUMENTS

2006/0082505 A1    4/2006   Baliarda et al.
2006/0164306 A1    7/2006   Chang et al.
2007/0100384 A1*   5/2007   Fischell et al. .................. 607/32
2007/0252773 A1   11/2007   Soler Castany et al.
2008/0062049 A1    3/2008   Soler Castany et al.

OTHER PUBLICATIONS

Soontornpipit, Pichitpong, "Design of Implantable Antennas for Communication with Medical Implants", (Thesis) *Utah State University*, 2002, 106 pgs.

* cited by examiner

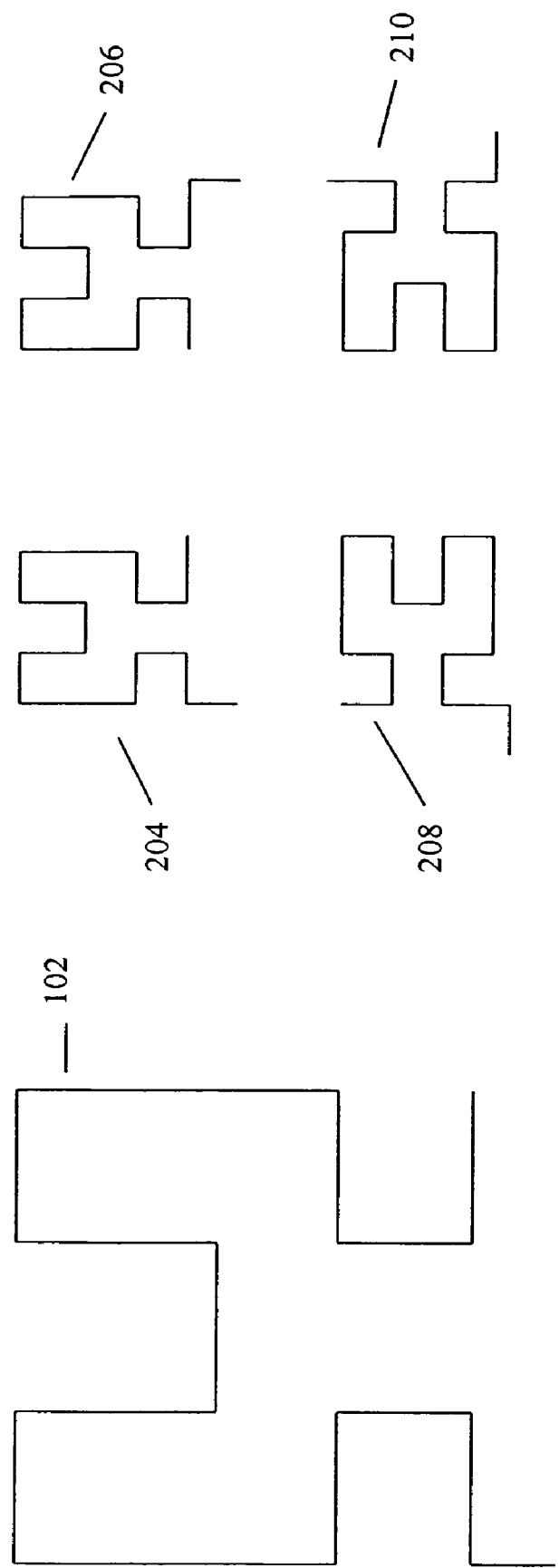

IMPLANTABLE MEDICAL DEVICE WITH FRACTAL ANTENNA

TECHNICAL FIELD

This subject matter pertains to implantable medical devices such as cardiac pacemakers and implantable cardioverter/defibrillators. In particular, the subject matter relates to an apparatus and method for enabling radio frequency telemetry in such devices using an antenna having a fractal pattern.

BACKGROUND

Implantable medical devices, including cardiac rhythm management devices such as pacemakers and implantable cardioverter/defibrillators, may have the capability to communicate data with what may be called an external programmer via a radio frequency telemetry link. A clinician may use an external programmer to program the operating parameters of an implanted medical device. For example, the pacing mode and other operating characteristics of a pacemaker may be modified after implantation of the pacemaker into the body in this manner. Modern implantable devices may also include the capability for bidirectional communication so that information may be transmitted to the external programmer from the implanted device for monitoring purposes. Data which may be transmitted from an implantable device to the external programmer may include various operating parameters and physiological data, either collected in real-time or stored from previous internal monitoring operations.

Telemetry systems for implantable medical devices utilize radio frequency energy to enable bidirectional communication between the implantable device and an external programmer. A radio frequency carrier may be modulated with either analog or digital information by amplitude shifting (i.e., AM [if analog] or ASK [if digital]), frequency shifting (i.e., FM [analog] or FSK [digital]), phase shifting (i.e., PM [analog] or PSK [digital]), or some combination of the above, such as Quadrature Amplitude Modulation (i.e., QAM). The external programmer transmits and receives the radio signal with an antenna.

In many previous systems the implanted antenna efficiency is very poor, and thus the antenna for the external device must be positioned in close proximity to the implanted device. In some previous systems, the implantable device and the external programmer communicate by generating and sensing a modulated electromagnetic field in the near-field region with the antennas of the respective devices inductively coupled together. The external antenna must therefore be close to the implantable device, typically within a few inches, in order for communications to take place. This requirement is inconvenient and limits the situations in which telemetry can take place.

While far-field RF telemetry has also been proposed, there exists a problem in the art of poor antenna efficiency. There also exists a problem with an implanted antenna having transmission field strengths that are not omni-directional (i.e., relatively similar strength in all directions) and the resulting antenna efficiency may depend upon the relative position of the body into which the device has been implanted. For example, an antenna that works well when the body is in a vertical position, may not have sufficient efficiency to operate when the body is in a horizontal position. The RF tuning circuits of some of the previous devices may also present a problem of maintaining adequate efficiency in the variety of possible device implant sites (different surrounding tissues have different dielectric constants), in the variety of different patient body types, and in a single patient over time, as the composition of the body into which it has been implanted changes with time, for example if a patient gains weight after the surgical insertion of a cardiac pacemaker.

SUMMARY

The present inventors have recognized that what is needed in the art is an implantable antenna that has a broadband characteristic with omni-directional field strength uniformity, small size, improved efficiency, and not requiring a dynamic adjustable tuning circuit.

The above noted problems are addressed with a fractal antenna implanted into body for transmitting modulated radio frequency information in a bi-directional fashion with an external device.

An implantable device is disclosed including a header coupled to an implantable housing, where the housing has an electronic circuit configured to communicate via a modulated radio frequency carrier, with a fractal antenna. The antenna is typically either within, on, or adjacent to the header and coupled to the electronic circuit in the implantable housing via conductive feed throughs. At least one conductive segment of the antenna forms at least one fractal pattern. In another embodiment the antenna is disposed within the header. In another embodiment the antenna is within a groove formed on the inner surface of the header. In yet another embodiment the antenna is covered with a material having a selected dielectric constant. In another embodiment the antenna is disposed on an outer surface of the header. In another embodiment the antenna is disposed within a groove formed on the outer surface of the header. In another embodiment the antenna is separated from the header. TECOTHANE® (Thermedics Inc., Woburn, Mass.) is an aromatic polyether-based thermoplastic polyurethane which has a dielectric constant of about 4.4 and is biocompatible so that it may be used as the composition of an implantable device header. With a header fabricated of TECOTHANE®, the capacitance seen by an antenna would be approximately four times greater than would be the case if the antenna and header were separated by air.

In addition to housing the antenna assembly, the header also typically provides electrical connections for leads or other circuits of the implantable device. The header assembly is typically affixed to the medical device by an adhesive or mechanical fasteners. In an embodiment the header only provides electrical connections, and the antenna connections and the antenna are in a separate structure attached to the housing which maybe referred to as a radome. In an embodiment the radome is located on the opposite side of the housing from the header to decrease or minimize the potential interference of the radio waves of the antenna with the electrical signals from the electronic device contained within the implantable housing and transmitted to leads attached to selected portions of the body into which the implantable device has been implanted.

In another embodiment the antenna may be formed as a part of a printed circuit board, where the printed circuit board may be a multi-level board having a ground plane at a selected distance from portion of the printed circuit board forming the fractal pattern. The printed circuit board may be covered with a bio-compatible coating such as polytetrafluoroethylene (PTFE), expanded polytetrafluoroethylene (ETFE), polyetheretherketone (PEEK), parylene, silicone, polyurethane, aromatic polyether thermoplastics or glass. TECOTHANE®

(Thermedics Inc., Woburn, Mass.) is an aromatic polyether-based thermoplastic polyurethane that is employed in one embodiment.

In another embodiment the antenna is formed of a bent conductive wire which may be formed of a bio-compatible material such as titanium (Ti), platinum (Pt), iridium (Ir), osmium (Os), rhodium (Rh), niobium (Nb), gold (Au), silver (Ag), stainless steel and various combinations. The wire may have a circular cross section. Alternatively, the antenna may be formed of a sheet of conductive material stamped into the selected fractal pattern. The stamped pattern may then be folded, bent, or formed into a three dimensional form. The sheet of conductive material may be sculpted, bent, hammered, heat treated, laser formed, stamped, punched, or etched to form the selected fractal pattern. The antenna may be formed of a conductive material that is twisted, folded, molded, cast, milled, cut, sawed, wire electric discharge machining (EDM), or plunger EDM to form the selected fractal pattern.

In yet another embodiment the antenna may be formed in the shape of a conductive stent, such as those used to keep arteries open, or used to anchor devices to a selected location in a body. In still another embodiment the antenna may be formed of a patterned metal foil on a glass substrate patterned by using photolithography and etching processes used in integrated circuit technology, or similar methods used in forming magnetic devices or screen printing. The antenna may be formed in a three dimensional structure that is wrapped around the implantable housing. The implantable housing may be formed of a conductive material, and may form a ground plane which may be used as a reflector for the antenna.

Another embodiment includes an implantable medical device with a programmable or other electronic circuit such as a cardiac pacemaker, a cardioverter, or a defibrillator, in an implantable housing with a plurality of hermetic electrical feed throughs to an attached header on the housing. The housing may have an electronic circuit for two way communication via a modulated radio frequency carrier with an external device for programming, downloading history data logs, and recording and analyzing real time data from the implantable medical device. The header may have an antenna coupled to the electronic circuit including at least one conductive segment forming a fractal pattern. The antenna may have an electrical connection to the housing forming a ground reference plane for the antenna to improve range and integrity. The antenna may provide an omni-directional far field distribution, with a field distribution that varies by less than 6 db from a minimum to a maximum field strength at a preselected radius from the antenna in at least one plane. The antenna typically provides several resonant frequencies at which it is efficient at transmitting, with a preferred embodiment having at least two resonant bands including the ranges of 400-450 Mhz and 863-928 Mhz. The antenna typically provides uniform enough of a three dimensional far field distribution that the antenna efficiency does not significantly change when the medical device in a patient is in the vertical position, as may occur when a patient is active, or in the horizontal position, as may occur when a patient is asleep. An additional benefit that occurs in some embodiments with a fractal implantable antenna having a broadband response is the modulated radio frequency carrier may not need a tuning circuit, or at least not need a dynamic tuning circuit.

Other aspects will be apparent on reading the following detailed description and viewing the drawings that form a part thereof.

BRIEF DESCRIPTION OF THE DRAWINGS

FIG. 1 illustrates an antenna pattern;
FIG. 2 illustrates reduced and/or rotated copies of the antenna pattern.

DETAILED DESCRIPTION

Figure 3:
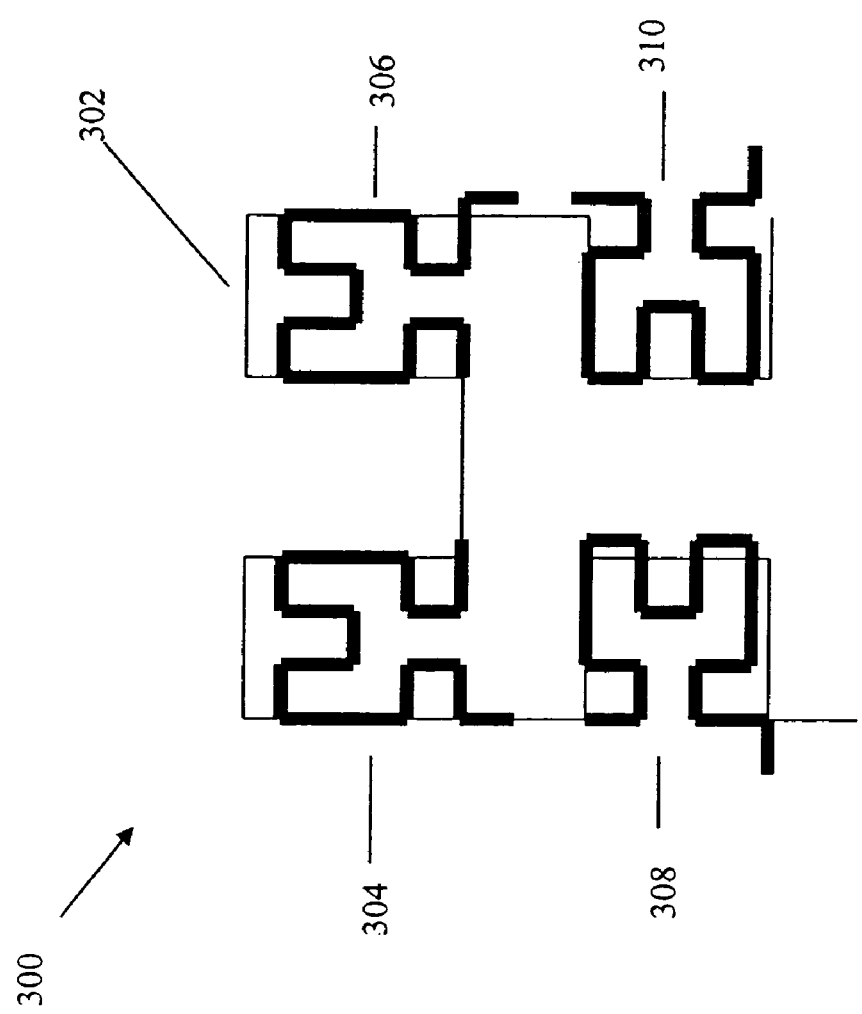
FIG. 3 illustrates forming an antenna pattern using smaller building blocks.

In the following detailed description, reference is made to the accompanying drawings that form a part hereof, and in which is shown, by way of illustration, specific embodiments in which the present subject matter may be practiced. These embodiments are described in sufficient detail to enable those skilled in the art to practice the subject matter, and it is to be understood that the embodiments may be combined, or that other embodiments may be utilized and that structural, mechanical, logical and electrical changes may be made without departing from the scope of the present subject matter. The following detailed description is, therefore, not to be taken in a limiting sense, and the scope of the present subject matter is defined by the appended claims and their equivalents.

As previously noted, conventional radio frequency (RF) telemetry systems used for implantable medical devices such as cardiac pacemakers may have an issue with either the uniformity of the RF transmission field over time, or related to the particular position of the antenna. Additional issues include the relatively large size, low antenna efficiency and the need to adjust the tuning of the antenna to respond to different required transmission bands and body changes. An antenna formed in a fractal shape may provide a broadband response that provides substantially uniform transmission strength in three dimensions (3D) without the need for a dynamic adjustable tuning circuit. Changes in transmission efficiency over time may be related to changes in the tuning circuit typically used in prior devices, changes in the environment of the antenna, such as a change in the weight of the patient in which the antenna is implanted, or changes in the dielectric constant of the implanted antenna's surroundings. Changes in position of the antenna may be related to the activity level of the patient into whom the antenna has been implanted, for example the horizontal position typically encountered during sleep will change the position of the antenna and in the case of many antenna types, results in a significant decrease in antenna transmission efficiency.

A fractal may be considered as a geometric object that has some or all of the following characteristics: a) having a self similar nature where the individual parts of the shape have a similar form or as the whole, but at a different scale or size; b) having a form that is irregular and remains irregular independent of the scale of examination; c) having a shape or a curve that repeats itself at any scale. An example of a fractal pattern may include a snowflake, which has the same six fold symmetry at macroscopic and at all microscopic levels.

In addition to having a benefit over prior implanted antenna devices in the uniformity of transmission efficiency with changes in the antenna surroundings and with changes in position, a fractal antenna may be smaller than other types of antenna, which may be a particular benefit in the field of implantable antennas, such as where the available space inside a body is minimal. Thus a fractal antenna is smaller, has better performance, and higher efficiency than other antenna types, and may have a relatively omni-directional broadband transmission.

Governmental regulatory agencies control which regions of the electro-magnetic spectrum are allowed for medical devices. Different geographic or political entities may have different allowed transmission bands. Previous antennas have dynamically adjustable tuning circuits to allow the antenna transmission bands to be adjusted to a chosen one band of the allowable regions. The present fractal antennas have multi-band transmission capability without the need for an additional adjustable tuning circuit, and thus may be used in different regions and at different transmission bands within a given region without having to separately provide a different antenna circuit for each case, easing manufacturing and inventory control, and thereby reducing the cost of the medical device.

A fractal antenna of a desired shape may be manufactured easily, inexpensively, reproducibly, and reliably, such as by fabricating a planar antenna on a printed circuit board (PCB), or etching fine lines in a thin sheet of metal as is done in the integrated circuit (IC) lead frame industry, or stamping a shape in a sheet of conductive material as is done in the IC packaging industry, or other easily imaged methods. An antenna with ground planes for reflection fixed at a specified distance from the antenna to improve the transmission efficiency may be formed using multi-layer PCBs, where standard electrical ground planes used for the electronic device industry. Thus, the formation of very fine lines in a small highly precise and reproducible antenna process may be enabled using processes from other industries.

To understand how much more efficient a fractal antenna is as compared to one of the current implantable device antenna, it is helpful to look at how antenna work in general. Any antenna operates by having a time-varying electrical current flow in a conductive material to produce a corresponding electromagnetic field that propagates through space in the form of electromagnetic waves. The total field produced by an antenna has what is known as a far-field component, where the magnitudes of the electric and magnetic fields vary inversely with distance from the antenna, and what is known as a near-field component, with field magnitudes varying inversely with higher powers of the distance. The field in the close vicinity of the antenna is due to the near-field component, also known as the induction field, while the field at greater distances is due solely to the far-field component, is known as the radiation field.

The near-field is a reactive field in which energy is stored and retrieved but results in no net energy outflow from the antenna unless a load is present in the field, coupled either inductively or capacitively to the antenna. The far-field is a radiating field that carries energy away from the antenna regardless of the presence of a load in the field. This energy loss appears to a circuit driving the antenna as a resistive impedance which is known as the radiation resistance. If the frequency of the radio frequency energy used to drive an antenna has a wavelength that is much greater than the length of the antenna, a negligible far-field component is produced. In order for a substantial portion of the energy delivered to the antenna to be emitted as far-field radiation, the wavelength of the driving signal should not be very much larger than the length of the antenna. At radio frequencies (RF), this tends to make simple antenna shapes fairly large as compared to the desired size for implantation into a human body.

An antenna most efficiently radiates energy if the length of the antenna is an integral number of half-wavelengths of the driving signal. As an example, a dipole antenna is a center-driven conductor that has a length equal to half the wavelength of the driving signal. Such a dipole antenna can be made, for example, of two lengths of conductive material arranged end to end with the cable from a transceiver coupled to each length of the dipole in the middle. An efficiently radiating resonant structure is formed if each length of the dipole is a quarter-wavelength long, so that the combined length of the dipole from end to end is a half-wavelength. A shorter antenna can produce a similar field configuration by utilizing a ground plane to reflect electromagnetic waves emitted by the antenna and thereby produce an image field. A monopole antenna includes a conductor with a length equal to one-quarter the wavelength of the driving signal situated with respect to a reflecting ground plane so that the total emitted and reflected field configuration resembles that of the dipole antenna. For example, for a carrier signal of 1 GHz, the wavelength in free space (i.e., not inside a living body) is approximately 32 cm. In free space, a half-wavelength dipole antenna would optimally be approximately 16 cm long, and a quarter-wavelength wavelength monopole antenna would optimally have a length approximately 8 cm with the housing, or other conductive surface, serving as a ground plane. Because the permittivity of body tissues is greater than that of free space, the corresponding optimum dipole and monopole antennas in the human body would be approximately half these lengths. A longer antenna length is needed for a lower frequency carrier, such as those typically assigned to medical devices, as noted above. Thus an antenna to be implanted into a human body using prior methods may be inconveniently large in order to have acceptable transmission efficiency.

In addition to the resonant frequency, antennas are also characterized by a quality factor (Q) and by impedance. The Q of an antenna is a measure of performance or quality of a resonator and can be conceptualized as a measure of energy loss per cycle (i.e., dissipation) as compared to the energy stored in the fields inside the resonator. Antenna impedance is the sum of a real component and an imaginary component, and may be between approximately 35 and 150 ohms.

Implantable antennas should be highly efficient and compact, but should also be bio-compatible. An antenna may be fabricated of a bio-compatible material such as titanium, niobium, platinum, iridium, stainless steel, gold, silver or other conductors having low resistance, or an alloy of platinum and iridium such as 90% platinum and 10% iridium. These bio-compatible materials are also used for electrical feed throughs for the housing containing the medical device circuitry, and thus the antenna may be integrated with the feed through with no welding or other means of attachment required. This may simplify the fabrication of the device, thus reducing cost and increasing reliability.

Non bio-compatible materials may be used if they are suitably sealed with a bio-compatible material such as poly-tetrafluoroethylene (PTFE), expanded polytetrafluoroethylene (ETFE), polyetheretherketone (PEEK), parylene, silicone, polyurethane, TECOTHANE®, aromatic polyether thermoplastics or glass. For example, a fractal antenna formed of copper conductors may be used by sealing the antenna in between glass plates. Alternatively, aluminum, copper or solder traces forming a fractal pattern on a printed circuit board (PCB) may be coated with silicone to make the assembly bio-compatible for implantation. In this illustrative example, the fractal pattern could be formed using silk screening or photolithography, which are well controlled and inexpensive.

In one embodiment, the antenna is formed on a bio-compatible substrate such as silicon or glass, using a non bio-compatible material such as copper, aluminum or lead tin alloy. The structure is made bio-compatible by hermetically sealing a second bio-compatible cover to the substrate, such as by glass-to-silicon anodic bonding, silicon-to-silicon fusion, glass frit melting, glass pre-form fusion, or other techniques. Using hermetic sealing permits use of conductive material having lower resistance. This reduces the antenna loss per cycle, as noted above, and increases the Q of the system. Moreover, the cost of non bio-compatible materials may be lower, and the ease of manufacture of non bio-compatible materials may be greater.

The fractal antenna may be planar, or it may alternatively be formed in a three dimensional shape. The antenna may be located in a header connected to the implantable housing containing the electronic circuitry. The header typically contains the electrical feedthroughs for the intravascular leads going from the electronic circuitry to a location away from the housing, such as within a heart chamber. Alternatively, the antenna may have a separate header structure in order to reduce possible issues with antenna-to-lead cross-talk or interference. A header used only for one or more antenna feedthroughs may be referred to as a radome. The radome may be on the opposite side of the housing from the lead-connection header to further decrease the possibility of interference between lead and antenna. In one embodiment, the header or radome is fabricated of insulative material, such as polyurethane resin, having a particular dielectric constant. As noted above, a particular specified dielectric constant may be used to adjust the size or length of the antenna. In one embodiment, the header is fabricated of a thermoplastic urethane, such as TECOTHANE®, an aromatic polyether-based hydrophilic thermoplastic polyurethane with a dielectric constant of about 4.4, made by Thermedics Inc., Woburn, Mass. For a header fabricated of TECOTHANE®, capacitance per unit antenna area may be about four times greater than if the antenna and header were separated by air. However, in general, an antenna in a radome of relative dielectric constant of about 4 only needs to be about ∕1;4 the size because the dielectric constant changes the electrical length of the antenna. If such a high capacitance results in unacceptable losses to the antenna, or if the antenna Q is too high for broadband use due to the high dielectric constant, an alternative material with a lower dielectric constant of 2.1 to 2.4 such as polytetrafluoroethylene (PTFE) may be used. A header fabricated of PTFE rather than thermoplastic urethane increases the radiation efficiency of the antenna by decreasing the capacitance between the antenna and the device housing. Other examples of materials with lower dielectric constants suitable for use as a header material include expanded polytetrafluoroethylene (ETFE) with a dielectric constant of 2.6, and polyetheretherketone (PEEK) with dielectric constant of 3.6.

In various examples, the antenna may be located within the header or radome, may be formed of uninsulated or insulated conductive materials, may be embedded in the walls of the housing or radome, may be separated from the housing by a particular distance, or may be wrapped around the housing. The housing may be formed of an insulator material or a conductive material. With a conductive housing, the antenna may have increased efficiency by using the housing as a reflector, as discussed previously. A preferred embodiment that decreases or minimizes space requirements but still allows for efficient radiation includes a wire antenna having a fractal pattern embedded within the header. In various embodiments, an etched conductive sheet fractal antenna is disposed in substantially parallel alignment with a curved surface of the conductive housing. As used herein, substantially parallel includes routing of the antenna such that, over at least a portion of the length of the antenna, the surface of the housing and the antenna are conformal and maintain a selected minimum distance. In certain examples, the antenna is a one-piece design integral to the implantable device.

In a preferred embodiment the fractal antenna is designed with a pattern such that its intrinsic impedance closely matches the RF circuitry in the implantable housing. This example minimizes the need for dynamically adjustable impedance matching circuitry as part of the implantable device, and the resulting device is simpler, more inexpensive and more reliable. In another preferred embodiment the fractal antenna is designed to have at least two transmission bands, such as at 400-450 MHz and 862-928 MHz, and not requiring a separate matching circuit for either band. In another preferred embodiment, the fractal antenna has a single signal feed point to obtain both of the two preferred transmission bands.

Fractal antennas typically have multiple resonant paths as a function of the repeating nature of the pattern, and thus are broadband radiators with multiple efficient transmission bands, while still being very compact and omni-directional. The small size is a function of the fractal pattern filling in the empty areas of the pattern with smaller sized copies of the larger pattern, thus having a space filling property that results in long antenna lengths in a small space or volume. In general, for a given surface area, the length of the antenna that can be placed in the given surface area improves at an exponential rate for each iteration of fractal pattern reduction, resulting in better antenna performance.

FIG. 1 shows an embodiment of an exemplary implantable fractal antenna base pattern, from which this particular illustrative embodiment of a fractal pattern for an antenna may be built. This particular pattern 102 has been picked purely for ease of illustration, and not as a representative embodiment for the present subject matter, or as representative of fractal patterns. The figure may be viewed as showing a bent wire antenna having a length. The antenna could equally well be viewed as a solid thin sheet of metal having a pattern cut, stamped, burned or other material removal method to form the illustrated cutout. Such a cutout antenna may be referred to as a slot antenna.

The pattern 102 has a length that will determine the wavelength bands in which the antenna will transmit efficiently. A dipole antenna will generally be most efficient at a wavelength that is about twice the length of the antenna, and could be varied by selecting different feedline points on the antenna. The pattern 102 may be viewed as being a geometrically larger version of the smaller similar patterns that will be discussed next. The pattern 102 will be seen to essentially be formed of a group of the smaller versions of itself.

FIG. 2 illustrates four smaller shapes 204, 206, 208 and 210, that are similar to pattern 102 of FIG. 1, in four different orientations. Pattern 204 has the same orientation as pattern 102, at a smaller scale. Pattern 206 is a mirror image around a vertical axis of pattern 204. Pattern 208 is a clockwise rotated mirror image of pattern 204, while pattern 210 is a counterclockwise rotation of pattern 204, all at the same level of reduction of scale. The larger form of pattern 102 of FIG. 1 may be conceptualized as being formed of the four smaller patterns 204, 206, 208 and 210. The connection points of the four patterns 204, 206, 208 and 210 are to the open end of the particular pattern points to another one of the patterns.

FIG. 3 illustrates how the four small patterns 204, 206, 208 and 210 may be placed to form the larger pattern 102. The shown pattern 302, is a full scale copy of the pattern 102 of FIG. 1, while the patterns 304, 306, 308 and 310 are full scale copies of patterns 204, 206, 208 and 210 of FIG. 2, with heavier lines to clarify how the small patterns can be placed to essentially form the larger similar pattern. This illustration shows how a repeating pattern on different scales may be used to form a fractal pattern, in which a series of different scale views of the pattern each reveal the same basic underlying structure. Such repeating patterns are how a fractal antenna may possess many resonance wavelengths.

Figure 4:
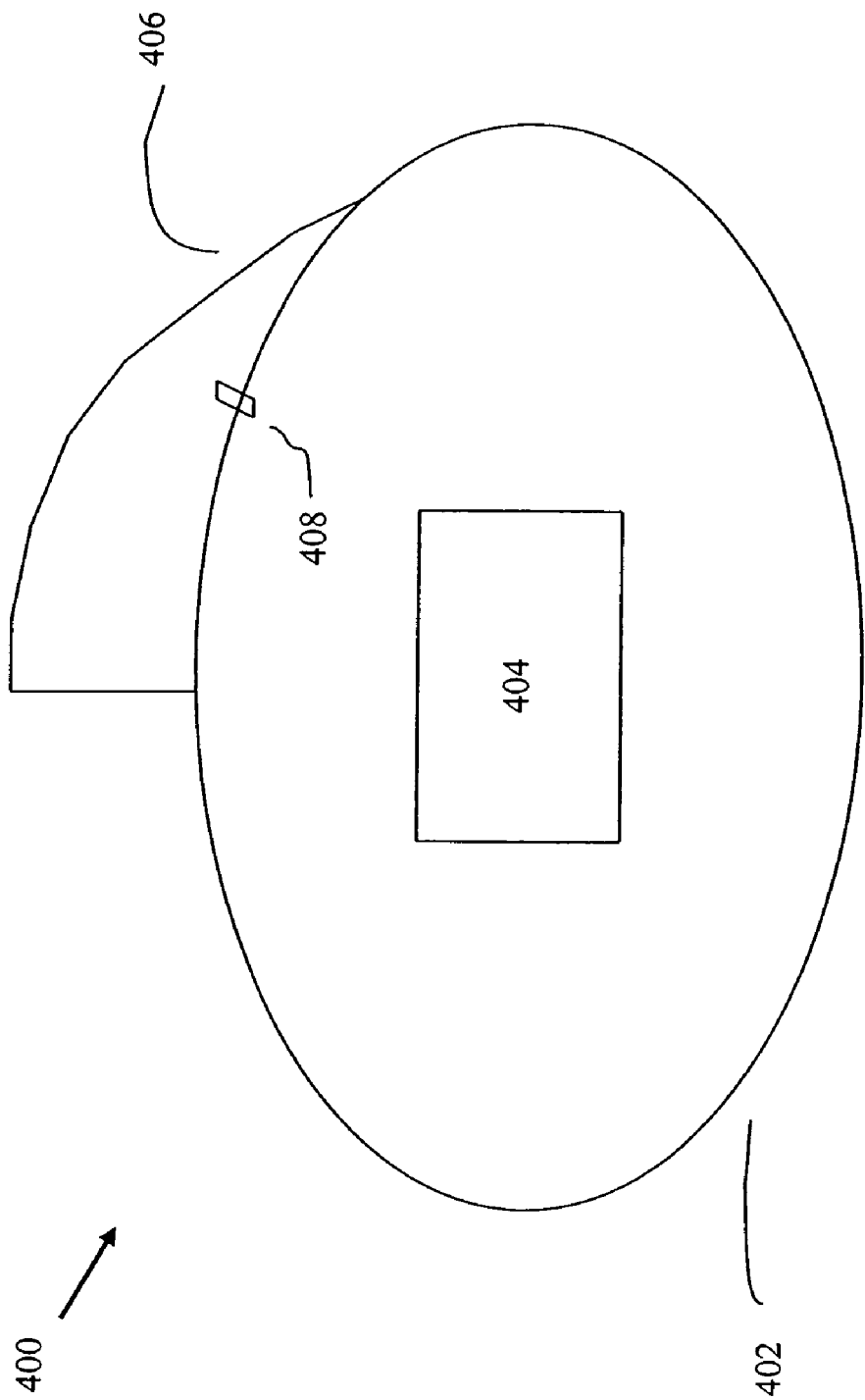
FIG. 4 illustrates an implantable device according to one embodiment of the present subject matter.

FIG. 4 is a illustrative view of an implantable device 400, having a housing 402, which may include a conductive surface over all or part of the surface of the housing 402, and typically contains electronic circuitry 404 for providing particular functionality to the device such as cardiac rhythm management, physiological monitoring, drug delivery, or neuromuscular stimulation as well as circuitry for providing radio frequency communications. The device 400 typically has a header 406 attached to the housing 402 to protect electrical feedthroughs 408 from direct contact with the surrounding body. Feedthrough 408 may be one of a plurality of feedthroughs, which provide an electrically isolated conductive path through a wall of housing 402, as well as providing a hermetic seal for the environment within the interior of housing 402. The portion of the housing 402 containing the feedthroughs typically includes certain regions of insulating material to avoid shorting the feedthroughs. There will typically be one feedthrough 408 for each electrical signal that leaves the housing 402, such as for being delivered to or from one or more leads for connecting to portions of a patients heart to serve intrinsic electrical heart signals or to provide suitable electrical pulses for stimulating heart contractions or for connecting the circuitry 404 to an antenna located either inside or outside of the header 406. In an embodiment, housing 402 includes a shell formed of non-conductive material and a conductive film or foil to serve as a ground plane for an antenna.

Figure 5:
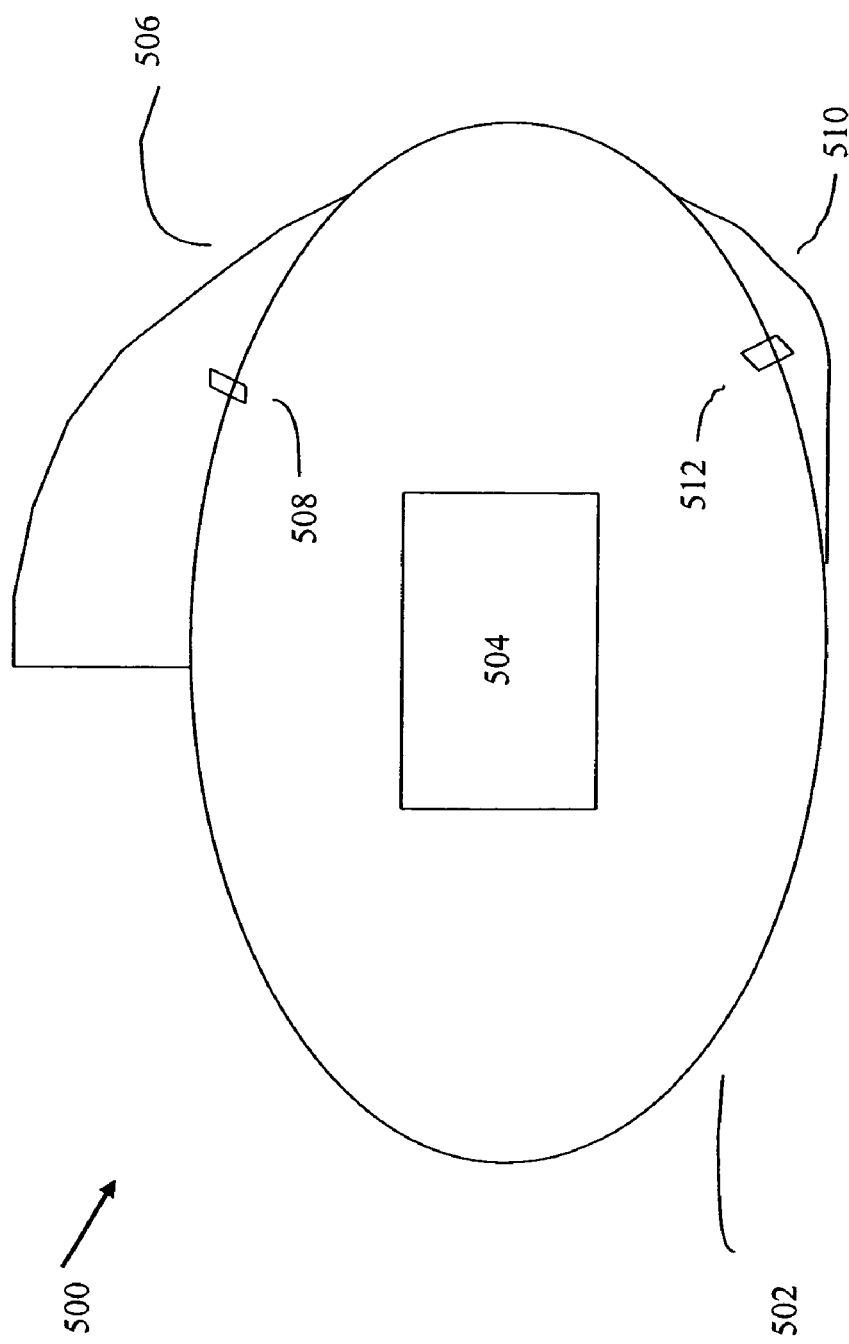
FIG. 5 illustrates an alternative design of implantable device according to one embodiment of the present subject matter.

FIG. 5 illustrates a view of an implantable medical device 500 configured to decrease potential cross talk and interference issues with having antenna feedthroughs in close proximity to lead feedthroughs. Housing 502 contains circuitry 504 and header 506 for lead feedthroughs 508. In this example, the housing 502 also has radome 510 for antenna feedthroughs 512 on an opposite surface of the housing 502. The illustration shows the radome 510 as positioned on the same half of the housing 502 as the header 506, but the radome 510 may be positioned at any location on the housing 502, including diametrically opposite the header 506 or immediately adjacent to header 506. Header 506 and radome 510 are coupled to a surface of housing 502, and are formed of various materials including a molded polymer such as thermoplastic polyurethane.

In FIGS. 4 and 5, a fractal antenna may be located completely inside the header 406 or radome 510, either disposed in or on a surface of header 406, or on a surface of housing 402 covered by the header 406, or suspended off of a conductive or other surface of either the header 406 or the housing 402 by a selected distance, or various other locations. Alternatively, the antenna may be located outside the header or radome, and disposed on the outer wall of the radome 510 or the housing 502, or conformally positioned around all or portions of the housing 502, or located at a distance from the housing 502. For example, an electrical lead, a lead bore hole, or other conductive structure, located near the antenna may alter the radiation pattern transmitted by the antenna. In an embodiment, the antenna is positioned within the header at a distance no closer than approximately 25 mils from a conductor that is electrically isolated from the antenna.

All of the described embodiments have various advantages and disadvantages. There are many potential locations for the fractal antenna or antennas depending upon the particular use conditions. A particular embodiment of a fractal antenna that is remote from the housing 502 is discussed in the next section with reference to FIG. 6. Other embodiments of locations for the fractal antenna include inside a groove cut in the surface of the radome 510 and then filled with a dielectric material having a selected dielectric constant. The groove may be formed by molding or by a materials removal process after molding, such as milling. In one embodiment, the encapsulating material includes silicone or other bio-compatible material suitable for implantation. The encapsulating material provides physical protection for the antenna and provides a suitable and more predictable dielectric constant for the antenna environment. However, a high dielectric constant results in an increased Q of the antenna, which may result in inefficiencies that reduce the radiation efficiency. These losses become larger as the frequency of the driving signal increases and as the capacitance increases. One way to decrease the value of the capacitance is to increase the distance separating the antenna from the device housing. This is discussed in the next section with reference to FIG. 6. The capacitance resulting from the proximity of the antenna and the conductive surface is a function of the dielectric constant of the header, the physical separation and the carrier frequency. Capacitance can be reduced, for example, by selection of a header material having a lower dielectric constant.

Reducing the capacitive loading of an antenna, however, also decreases its effective electrical length, thus affecting the ability to operate at lower frequencies. In order to increase the effective electrical length, the antenna may be coated with a film of high dielectric material. The film, in various embodiments, includes an oxide such as titanium oxide, aluminum oxide and barium strontium titanate. The film provides a uniformly high dielectric constant as seen by the antenna. The film can be formed, for example but not by way of limitation, by deposition of films and coatings, film growth or epitaxy, including for example, deposition by sputtering, vacuum deposition, laser deposition, chemical vapor deposition, molecular epitaxy, atomic epitaxy, ion epitaxy, chemical beam epitaxy, ion and electron beam-assisted deposition, ion plating, electrodeposition, electroplating and spray coating. The antenna may include a conductive material in the form of a wire, patterned planer materials such as foil, sheet metal, or other conductive surfaces formed by semiconductor fabrication techniques using a substrate, such as integrated circuits and PCBs.

Figure 6:
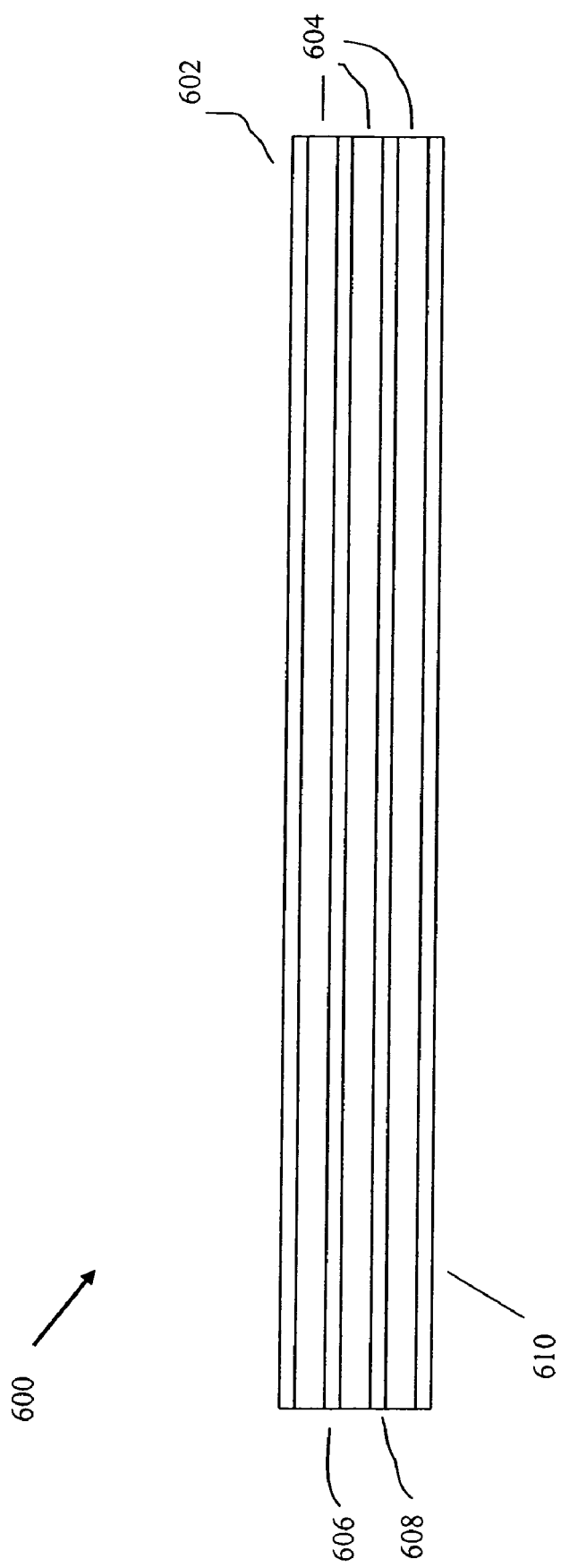
FIG. 6 illustrates a printed circuit board embodiment of the antenna.

FIG. 6 illustrates a cross sectional view of a fractal antenna structure formed on a PCB 600. In an illustrative example, the top conductive layer 602 is formed into a selected fractal pattern, such as pattern 300 of FIG. 3, on top of one of a plurality of insulative layers 604, which may have electrically conductive vias for selective interconnection of the conductive layers 602, 606, 608 and 610. Conductive layer 606 may be a ground plane used as a reflector for the antenna formed on layer 602. Conductive layer 608 may be used for electrically connecting a signal feed line to various locations in the pattern formed in layer 602. Different signal feed locations affect the radiated signal properties, such as the best resonant frequency. Conductive layer 610 in this illustrative embodiment may be used as a additional interconnect layer to enable signal line crossing with reduced signal cross talk and interference. Other layer assignments and number of conductive layers are envisioned depending upon the design of the overall system having the antenna. For example, the conductive layer 608 may be used as the ground plane reflector for the fractal pattern antenna of layer 602 rather than using conductive layer 606, if the proper separation of the ground plane from the antenna better matches the spacing provided by conductive layer 608. In one embodiment, the antenna is formed in the PCB 600, with the ground plane the conductive housing located at a calculated distance, in one embodiment 2 millimeters. In another embodiment the fractal antenna would be positioned in a perpendicular plane to the surface of the implantable device housing forming the ground plane.

The embodiments discussed above using a fractal antenna for RF communications from an implanted medical device include a remote programmer or other external device coupled to an antenna, which may also be a fractal antenna similar to the implanted antenna already discussed. The use of a fractal antenna at the external device may be beneficial due to the broadband properties and the omni-directionality of the described fractal antenna.

The embodiments discussed above have the benefits of providing an antenna having a large effective size due to the space filling properties of the fractal design, which in turn results in a large bandwidth, which in turn results in a system that has both a better response to changes in the antenna environment such as tissue detuning, and a higher efficiency, which translates into increased range. Benefits include omni-directional radiation pattern and 3D patterns improving the antenna's response to changes in orientation of the antenna due to body motion and position changes. Further advantages include the ease of adapting the antenna to local regulations on RF bands for medical transmissions, as well as the ability to change bands dynamically to obtain better transmission characteristics within a given locality as the patient moves about.

The described embodiments further include the use of various ground plane reflectors such as a separate conductive layer of a PCB, or the use of the medical device housing, and the ability to use different or multiple signal feed locations to adjust the transmission characteristics. The use of fractal antenna enables impedance matching of the antenna to the driving electronic circuitry without the need for dynamically adjustable matching or tuning circuits, and the small size of the fractal antenna allows the use of multiple antenna either inside or outside of the header/radome. The antenna may be formed of wires, sheet metal or solid conductors and may have either a flat shape, a flat shape that has been bent or formed, or a three dimensional shape. The use of well known and inexpensive electronic manufacturing processes used in the IC and PCB technologies, as well as the use of standard machining and milling methods results in smaller, more efficient, better performing and less expensive antenna. The use of either bio-compatible materials, or the use of non bio-compatible materials that are hermetically sealed results in greater flexibility and improved performance.

CONCLUSION

The above description is intended to be illustrative, and not restrictive. Many other embodiments will be apparent to those of skill in the art upon reviewing the above description. The scope of the present invention should not be limited to the described embodiments, and is set forth in the following claims.

What is claimed is:

1. A device, comprising:
    a header coupled to an implantable housing, the housing having an electronic circuit configured to communicate via a modulated radio frequency carrier;
    an antenna, at least a portion of the antenna disposed within, on, or adjacent the header and coupled to the electronic circuit; and
    the antenna including at least one conductive segment forming at least one selected self-similar fractal pattern,
    wherein the antenna is disposed at a fixed distance away from the header and the implantable housing, and
    wherein the antenna is disposed on a printed circuit board.

2. The device of claim 1, wherein the antenna is disposed within the header.

3. The device of claim 1, wherein the antenna is disposed on a surface of the header.

4. The device of claim 3, wherein the antenna is disposed within a groove formed on the surface of the header.

5. The device of claim 3, wherein the antenna is covered with a dielectric material having a selected dielectric constant.

6. The device of claim 3, wherein the antenna has a shape that is conformal to a portion of the surface of at least one of the header and the implantable housing.

7. The device of claim 1, wherein the printed circuit board is covered with a bio-compatible coating selected from the list including polytetrafluoroethylene (PTFE), expanded polytetrafluoroethylene (ETFE), polyetheretherketone (PEEK), parylene, silicone, polyurethane, aromatic polyether thermoplastics and glass.

8. An implantable medical device, comprising:
    a programmable electronic circuit configurable to perform as at least one of a cardiac pacemaker, a cardioverter, and a defibrillator, disposed in an implantable housing with a plurality of hermetic electrical feed throughs to a header;
    the housing having an electronic circuit configured to perform two way communication via a modulated radio frequency carrier with an external device capable of at least one of programming the implantable medical device, downloading history data logs from the implantable medical device, and recording and analyzing real time data from the implantable medical device; and
    an antenna, at least a portion of the antenna disposed within, on, or adjacent the header, and coupled to the electronic circuit and including at least one conductive segment forming a self-similar fractal pattern,
    wherein the antenna has at least two resonant frequencies.

9. The device of claim 8, wherein the antenna is configured to provide far field distribution that varies by less than 6 db in at least one plane from a minimum to a maximum field strength at a preselected radius from the antenna.

10. The device of claim 8, wherein the antenna has a broadband response and the electronic circuit in two way communication via the modulated radio frequency carrier does not include an adjustable tuning circuit.

11. A device, comprising:
    an antenna having at least a portion of the antenna shape in the form of a self-similar fractal pattern for communicating between a first electrical device implanted inside a body and a second device that is external to the body,
    wherein the antenna is implanted inside the body and coupled to the first electrical device via a non-conductive radome, and
    wherein the antenna uses the surface of the first electrical device as a ground reference plane.

12. The device of claim 11, wherein the radome is formed of a plastic having a selected dielectric constant.

13. The device of claim 12, wherein the radome is formed of TECOTHANE®, an aromatic polyether-based thermoplastic polyurethane.

14. The device of claim 11, wherein the radome is located on a surface of the electrical device at a point opposite to an electrical connection header location.

15. A device, comprising:
- an implantable housing including an electronic circuit configured to communicate via a modulated radio frequency carrier;
- at least one header coupled to the housing including a plurality of electrical signal feed throughs;
- at least one radome coupled to the housing including at least one antenna feed through; and
- the at least one antenna including at least one conductive segment forming a self-similar fractal pattern,
- wherein the at least one radome is located opposite the at least one header.

16. The device of claim 15, wherein the at least one radome is formed of a plastic material having a dielectric constant of from 4.0 to 7.0.

17. The device of claim 15, wherein the at least one radome is formed of TECOTHANE®, an aromatic polyether-based thermoplastic polyurethane.

* * * * *